(12) United States Patent
Tai et al.

(10) Patent No.: US 8,003,112 B2
(45) Date of Patent: Aug. 23, 2011

(54) MENINGOCOCCAL AND PNEUMOCOCCAL CONJUGATE VACCINE AND METHOD OF USING SAME

(75) Inventors: Stanley Shih-Peng Tai, Rockville, MD (US); Che-Hung Robert Lee, Silver Spring, MD (US)

(73) Assignees: Howard University, Washington, DC (US); The United States of America as represented by the Secretary, Department of Health and Human Services; National Institutes of Health, Office of Technology Transfer, Washington, DC (US)

( * ) Notice: Subject to any disclaimer, the term of this patent is extended or adjusted under 35 U.S.C. 154(b) by 0 days.

(21) Appl. No.: 12/425,232

(22) Filed: Apr. 16, 2009

(65) Prior Publication Data

US 2010/0266625 A1    Oct. 21, 2010

(51) Int. Cl.
*A61K 39/385*    (2006.01)
*A61K 39/116*    (2006.01)
*A61K 39/02*    (2006.01)
*A61K 39/00*    (2006.01)
*A61K 39/09*    (2006.01)
*C07H 3/00*    (2006.01)

(52) U.S. Cl. ............. 424/197.11; 424/234.1; 424/203.1; 424/184.1; 424/244.1; 424/250.1; 424/242.1; 424/831; 536/123.1

(58) Field of Classification Search ........................ None
See application file for complete search history.

(56) References Cited

U.S. PATENT DOCUMENTS

| | | | |
|---|---|---|---|
| 4,356,170 A | 10/1982 | Jennings et al. | |
| 5,773,007 A | 6/1998 | Penney et al. | |
| 5,849,301 A | 12/1998 | Lees | |
| 6,756,040 B2 | 6/2004 | Peetermans et al. | |
| 2003/0035806 A1* | 2/2003 | D'Ambra et al. | 424/184.1 |
| 2003/0068336 A1 | 4/2003 | Ryall | |
| 2005/0002948 A1* | 1/2005 | Ryall | 424/184.1 |
| 2007/0065462 A1* | 3/2007 | Ryall | 424/238.1 |
| 2007/0141084 A1 | 6/2007 | Lee et al. | |

FOREIGN PATENT DOCUMENTS

WO    2005/037320 A2    4/2005

OTHER PUBLICATIONS

A.E. Tutton. "The Isolation of Hydrazine." Nature, 1891, 1105, pp. 205-206.
A. Bartoloni et al., "Immunogenicity of Meningococcal B Polysaccharide Conjugated to Tetanus Toxoid or CRM197 Via Adipic Acid Dihydrazide." Vaccine, 1995, vol. 13, No. 5, pp. 463-470.
Z. Guo et al., "Protein-Polysaccharide Conjugation." Methods in Molecular Medicine, Meningococcal Vaccines: Methods and Protocols, 2001, Humana Press Inc., Totowa N.J., vol. 66, pp. 49-54.
H. Jennings et al., "Immunochemistry of Groups A, B, and C Meningococcal Polysaccharide-Tetanus Toxoid Conjugates." Journal of Immunology, 1981, vol. 127, No. 3, pp. 1011-1018.
E. Konadu et al., "Phase 1 and 2 Studies of *Salmonella enterica* Serovar Paratyphi A O-Specific Polysaccharide-Tetanus Toxoid Conjugates in Adults, Teenagers, and 2- to 4-Year-Old Children in Vietnam." Infection and Immunity, Mar. 2000, vol. 68, No. 3, pp. 1529-1534.
C.-J Lee et al., "Quality Control of Polyvalent Pneumococcal Polysaccaride-Protein Conjugate Vaccine by Nephelometry." Biologicals, 2002, vol. 30, pp. 97-103.
A. Lees et al., "Activation of Soluble Polysaccharides with 1-Cyano-4-Dimethylaminopyridinium Tetrafluoroborate for Use in Protein-Polysaccharide Conjugate Vaccines and Immunological Reagents." Vaccine, 1996, vol. 14, No. 3, pp. 190-198.
D. Shafer et al., "Activation of Soluble Polysaccharides with 1-Cyano 4-Dimethylaminopyridinium Tetrafluoroborate (CDAP) For Use in Protein-Polysacharides Conjugate Vaccines and Immunological Reagents. II. Selective Crosslinking of Proteins to CDAP-Activated Polysaccharides." Vaccine, 2000, vol. 18, pp. 1273-1281.
International Application No. PCT/US2010/031083, Notification of Transmittal of the International Search Report and the Written opinion of the International Searching Authority, or the Declaration, date of mailing Aug. 6, 2010, 7 pages.

* cited by examiner

*Primary Examiner* — S. Devi
(74) *Attorney, Agent, or Firm* — Fitch, Even, Tabin & Flannery

(57) ABSTRACT

This disclosure relates to vaccine formulations comprising an immunogenic composition for inducing antibodies to both *S. pneumoniae* and *N. meningitides* in a subject. In a preferred aspect, the immunogenic composition comprises covalently conjugated recombinant PsaA ("rPsaA") from *S. pneumoniae* and capsular polysaccharide from *N. meningitidis* serogroup C. This disclosure further relates to methods for producing the immunogenic composition as well as methods for their use.

5 Claims, 4 Drawing Sheets

FIG. 1

```
GATCCTAGCG GAAAAAAGA TACAACTTCT GGTCAAAAAC TAAAAGTTGT⁵⁰
TGCTACAAAC TCAATCATCG CTGATATTAC TAAAAATATT GCTGGTGACA¹⁰⁰
AAATTGACCT TCATAGTATC GTTCCGATTG GGCAAGACCC ACACGAATAC¹⁵⁰
GAACCACTTC CTGAAGACGT TAAGAAAACT TCTGAGGCTA ATTTGATTTT²⁰⁰
CTATAACGGT ATCAACCTTG AAACAGGTGG CAATGCTTGG TTTACAAAAT²⁵⁰
TGGTAGAAAA TGCCAAGAAA ACTGAAACA AAGACTACTT CGCAGTCAGC³⁰⁰
GACGGCGTTG ATGTTATCTA CCTTGAAGGT CAAAATGAAA AAGGAAAAGA³⁵⁰
AGACCCACAC GCTTGGCTTA ACCTTGAAAA CGGTATTATT TTTGCTAAAA⁴⁰⁰
ATATCGCCAA ACAATTGAGC GCCAAAGACC CTAACAATAA AGAATTCTAT⁴⁵⁰
GAAAAAAATC TCAAAGAATA TACTGATAAG TTAGACAAAC TTGATAAAGA⁵⁰⁰
AAGTAAGGAT AAATTTAATA AGATCCCTGC TGAAAAGAAA CTCATTGTAA⁵⁵⁰
CCAGCGAAGG AGCATTCAAA TACTTCTCTA AAGCCTATGG TGTCCCAAGT⁶⁰⁰
GCTTACATCT GGGAAATCAA TACTGAAGAA GAAGGAACTC CTGAACAAAT⁶⁵⁰
CAAGACCTTG GTTGAAAAAC TTCGCCAAAC AAAAGTTCCA TCACTCTTTG⁷⁰⁰
TAGAATCAAG TGTGGATGAC CGTCCAATGA AAACTGTTTC TCAAGACACA⁷⁵⁰
AACATCCCAA TCTACGCTCA AATCTTTACT GACTCTATCG CAGAACAAGG⁸⁰⁰
TAAAGAAGGC GACAGCTACT ACAGCATGAT GAAATACAAC CTTGACAAGA⁸⁵⁰
TTGCTGAAGG ATTGGCAA⁸⁶⁸
```

* The underlining indicates the position of BamHI and HindIII sites at the 5' and 3' ends, respectively.

FIG. 2

| | | | |
|---|---|---|---|
| MKYLLPTAAA | GLLLLAAQPA | MAMDIGINSD | PSGKKDTTSG |
| QKLKVVATNS | IIADITKNIA | GDKIDLHSIV | PIGQDPHEYE |
| PLPEDVKKTS | EANLIFYNGI | NLETGGNAWF | TKLVENAKKT |
| ENKDYFAVSD | GVDVIYLEGQ | NEKGKEDPHA | WLNLENGIIF |
| AKNIAKQLSA | KDPNNKEFYE | KNLKEYTDKL | DKLDKESKDK |
| FNKIPAEKKL | IVTSEGAFKY | FSKAYGVPSA | YIWEINTEEE |
| GTPEQIKTLV | EKLRQTKVPS | LFVESSVDDR | PMKTVSQDTN |
| IPIYAQIFTD | SIAEQGKEGD | SYYSMMKYNL | DKIAEGLAKL |
| AAALEHHHHH | H | | |

* The amino acid sequence was deduced from the sequence of closed *psaA* fragment in expression vector pET22b(+). The underlined amino acids are the sequence of rPsaA and the other residues at the N- and C- were deduced from the vector.

FIG. 3

Lane 1. SDS-polyacrylamide gel electrophoresis of induced rPsA in crude lysate of *E. coli* BL21(DE3)(pST648).

Lane 2. SDS-polyacrylamide gel electrophoresis of purified rPsA. Proteins in SDS-PAGE were visualized by staining with coomassie blue.

Lane 3. Western blot analysis of purified rPsaA using anti-poly-histidine monoclonal antibodies (1:200 dilutions). (lane 2) of purified His-tagged rPsaA.

SEQUENCE LISTING

```
<160> NUMBER OF SEQ ID NOS: 4

<210> SEQ ID NO 1
<211> LENGTH: 331
<212> TYPE: PRT
<213> ORGANISM: Streptococcus pneumoniae

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Met Asp Ile Gly Ile Asn Ser Asp Pro Ser
            20                  25                  30

Gly Lys Lys Asp Thr Thr Ser Gly Gln Lys Leu Lys Val Val Ala Thr
        35                  40                  45

Asn Ser Ile Ile Ala Asp Ile Thr Lys Asn Ile Ala Gly Asp Lys Ile
    50                  55                  60

Asp Leu His Ser Ile Val Pro Ile Gly Gln Asp Pro His Glu Tyr Glu
65                  70                  75                  80

Pro Leu Pro Glu Asp Val Lys Lys Thr Ser Glu Ala Asn Leu Ile Phe
                85                  90                  95

Tyr Asn Gly Ile Asn Leu Glu Thr Gly Gly Asn Ala Trp Phe Thr Lys
            100                 105                 110

Leu Val Glu Asn Ala Lys Lys Thr Glu Asn Lys Asp Tyr Phe Ala Val
        115                 120                 125

Ser Asp Gly Val Asp Val Ile Tyr Leu Glu Gly Gln Asn Glu Lys Gly
    130                 135                 140

Lys Glu Asp Pro His Ala Trp Leu Asn Leu Glu Asn Gly Ile Ile Phe
145                 150                 155                 160

Ala Lys Asn Ile Ala Lys Gln Leu Ser Ala Lys Asp Pro Asn Asn Lys
                165                 170                 175

Glu Phe Tyr Glu Lys Asn Leu Lys Glu Tyr Thr Asp Lys Leu Asp Lys
            180                 185                 190
```

```
Leu Asp Lys Glu Ser Lys Asp Lys Phe Asn Lys Ile Pro Ala Glu Lys
            195                 200                 205
Lys Leu Ile Val Thr Ser Glu Gly Ala Phe Lys Tyr Phe Ser Lys Ala
    210                 215                 220
Tyr Gly Val Pro Ser Ala Tyr Ile Trp Glu Ile Asn Thr Glu Glu Glu
225                 230                 235                 240
Gly Thr Pro Glu Gln Ile Lys Thr Leu Val Glu Lys Leu Arg Gln Thr
                245                 250                 255
Lys Val Pro Ser Leu Phe Val Glu Ser Ser Val Asp Asp Arg Pro Met
            260                 265                 270
Lys Thr Val Ser Gln Asp Thr Asn Ile Pro Ile Tyr Ala Gln Ile Phe
        275                 280                 285
Thr Asp Ser Ile Ala Glu Gln Gly Lys Glu Gly Asp Ser Tyr Tyr Ser
    290                 295                 300
Met Met Lys Tyr Asn Leu Asp Lys Ile Ala Glu Gly Leu Ala Lys Leu
305                 310                 315                 320
Ala Ala Ala Leu Glu His His His His His His
                325                 330
```

<210> SEQ ID NO 2
<211> LENGTH: 994
<212> TYPE: DNA
<213> ORGANISM: Streptococcus pneumoniae

<400> SEQUENCE: 2

```
atgaaatacc tgctgccgac cgctgctgct ggtctgctgc tcctcgctgc ccagccggcg      60
atggccatgg atatcggaat taattcggat cctagcggaa aaaagataca aacttctggt     120
caaaaactaa agttgttgc tacaaactca atcatcgctg atattactaa aaatattgct      180
ggtgacaaaa ttgaccttca tagtatcgtt ccgattgggc aagacccaca cgaatacgaa     240
ccacttcctg aagacgttaa gaaaacttct gaggctaatt tgattttcta taacggtatc     300
aaccttgaaa caggtggcaa tgcttggttt acaaaattgg tagaaaatgc aagaaaact    360
gaaaacaaag actacttcgc agtcagcgac ggcgttgatg ttatctacct tgaaggtcaa     420
aatgaaaaag aaaagaaga cccacacgct tggcttaacc ttgaaaacgg tattattttt     480
gctaaaaata tcgccaaaca attgagcgcc aaagacccta acaataaaga attctatgaa     540
aaaaatctca agaatatac tgataagtta gacaaacttg ataagaaag taaggataaa      600
tttaataaga tccctgctga aaagaaactc attgtaacca gcgaaggagc attcaaatac     660
ttctctaaag cctatggtgt cccaagtgct tacatctggg aaatcaatac tgaagaagaa     720
ggaactcctg aacaaatcaa gaccttggtt gaaaaacttc gccaaacaaa agttccatca     780
ctctttgtag aatcaagtgt ggatgaccgt ccaatgaaaa ctgtttctca agacacaaac     840
atcccaatct acgctcaaat ctttactgac tctatcgcag aacaaggtaa agaaggcgac     900
agctactaca gcatgatgaa atacaaccct gacaagattg ctgaaggatt ggcaaagctt     960
gcggccgcac tcgagcacca ccaccaccac cact                                 994
```

<210> SEQ ID NO 3
<211> LENGTH: 26
<212> TYPE: DNA
<213> ORGANISM: Artificial Sequence
<220> FEATURE:
<223> OTHER INFORMATION: Forward primer

<400> SEQUENCE: 3

```
gggatcctag cggaaaaaaa gataca                                          26

<210> SEQ ID NO 4
<211> LENGTH: 27
<212> TYPE: DNA
<213> ORGANISM: Artificial Sequence
<220> FEATURE:
<223> OTHER INFORMATION: Reverse primer

<400> SEQUENCE: 4
gcaagctttg ccaatccttc agcaatc                                         27
```

MENINGOCOCCAL AND PNEUMOCOCCAL CONJUGATE VACCINE AND METHOD OF USING SAME

FIELD OF THE INVENTION

This disclosure relates to vaccine formulations that include an immunogenic composition for inducing antibodies to the *S. pneumoniae* PsaA protein and *N. meningitidis* capsular polysaccharide. This disclosure further relates to methods for producing the immunogenic composition as well as methods for their use.

BACKGROUND OF THE INVENTION

Status of current pneumococcal vaccines. *S. pneumoniae* is a gram-positive encapsulated diplococcus. Capsule, a layer of polysaccharide (PS) surrounding the bacterial cell, is a major virulence factor of *S. pneumoniae*. Based on the differences in structure and immunological response to capsular polysaccharide, *S. pneumoniae* can be divided into more than 90 different serotypes. Capsular polysaccharides are the base for the currently used vaccines. The FDA has approved two types of pneumococcal vaccines for use in humans: a 23-valent PS vaccine and a 7-valent PS/protein conjugate vaccine. The former is comprised of capsular polysaccharide purified from 23 different serotypes of *S. pneumoniae*, which account for almost 89 percent of disease cases. PNEUMOVAX® (Merck) is an example of this group of vaccines. However, PS elicits type-specific antibodies. Antibodies raised for one serotype do not provide protection against infection of other serotypes. The efficacy of the 23-valent vaccine is limited. Furthermore, PS is a T-cell independent antigen which induces short-term immunity without immune memory and is not effective in children younger than two years of age (Greenwood B M et al., Trans R Soc Trop Med Hyg, 1980, 74:756-760). It is only recommended for high risk groups, such as the elderly and persons with underlying disease. A recently approved pneumococcal vaccine is a mixture of conjugates of 7 different individually prepared capsular polysaccharides covalently linked with carrier protein $CRM_{197}$, which is a non-toxic and immunologically cross-reactive mutant of diphtheria toxin (Uchida et al, J. Biol. Chem. 248:3838-3844, 1973) and a component of the pediatric DPT (Diphtheria-Tetanus-Pertussis toxin) vaccine. Upon conjugation to a carrier protein, the otherwise T-cell independent PS becomes a T-cell dependent antigen by obtaining the immunological property of the protein. (Schneerson R et al., J Exp Med 1980, 152:361-376). The conjugate induces long-lasting immunity with immune memory and is effective in young infants. The 7 serotypes were selected for their prevalence in pediatric diseases. A conjugate vaccine of 7 pneumococcal capsular PS (PCV7) with $CRM_{197}$ (Wyeth) is the only vaccine of this family that is commercially available. It is only prescribed for use in the prevention of pediatric invasive pneumococcal disease because of its high cost and limited supply. The drawback of these two families of vaccines is that they only provide protection against infection by the specific serotypes of *S. pneumoniae* that are included in the respective vaccine formulations.

Status of current meningococcal vaccine. *N. meningitidis* is a gram-negative, encapsulated diplococcus. At least 13 different serogroups have been identified based on the structure of capsular PS, but serogroups A, B, C, Y, and W-135 account for almost all cases of disease. Serogroup B organisms account for 46 percent of all cases, serogroup C for 45 percent of all cases, and serogroups W-135 and Y and strains that could not be serogrouped account for most of the remaining cases. Like *S. pneumoniae*, the major ingredient for meningococcal vaccines is capsular PS. Its vaccines can be divided into two families: the capsular PS vaccine and PS-protein conjugate vaccines. Three versions of PS vaccines are commercially available.

Quadrivalent PS vaccine (GlaxoSmithKline and Sanofi-Pasteur) is composed of capsular PS purified from serogroups A, C, Y, and W-135. It is expensive and not affordable for developing countries. Bivalent PS vaccine (GlaxoSmithKline and Sanofi-Pasteur) is composed of capsular PS purified from serogroups A and C. Trivalent PS vaccine (GlaxoSmithKline) is composed of capsular PS purified from serogroups A, C, and W-135. This vaccine has been used in the epidemics in the "Meningitis Belt" countries in Africa. Like pneumococcal vaccine, PS vaccine is not efficacious in children younger than two years of age. Such deficiency can be overcome by PS-protein conjugates.

Two types of meningococcal vaccine conjugates are commercially available or being developed. MENACTRA® (Sanofi-Pasteur) is the first quadrivalent conjugate meningococcal vaccine. It is a mixture of meningococcal polysaccharides (groups A, C, Y, and W135) conjugated with diphtheria toxoid. A monovalent meningococcal conjugate vaccine currently under development is a conjugate of serogroup C polysaccharide-diphtheria toxoid (Chiron and Wyeth), serogroup C PS-tetanus toxoid (Chiron, Baxter), and serogroup A PS-tetanus toxoid (PATH-SII). Preliminary results of clinical trials indicate these vaccines are efficacious.

With the burden of *S. pneumoniae* and *N. meningitidis* infection on the public health system at a global scale, it is desirable to have a single vaccine that is effective to prevent disease resulting from the infection of both pathogens.

SUMMARY

This disclosure provides an immunogenic composition for inducing an immune response to two different microorganisms, *S. pneumoniae* and *N. meningitidis*. This disclosure further provides an inoculum and/or vaccine comprising the immunogenic composition dispersed and/or dissolved in a pharmaceutically acceptable diluent. The vaccine includes at least one *N. meningitidis* capsular polysaccharide conjugated to a pneumococcal protein. In a preferred aspect, the immunogenic composition comprises recombinant PsaA ("rPsaA") from *S. pneumoniae* and capsular polysaccharide from *N. meningitidis* serogroup C. Pneumococcal protein acts as an antigen as well as a carrier protein for *N. meningitidis* capsular polysaccharide in the vaccine. Thus, the vaccine is effective for providing dual protection against infection by both *S. pneumoniae* and *N. meningitidis*.

Several pneumococcal proteins are universally found in all tested serotypes of *S. pneumoniae*, such as pneumococcal surface antigen A (PsaA), pneumococcal surface protein A (PspA), pneumococcal surface protein C (PspC), pneumolysin, and histidine-triad proteins. Studies have shown that these proteins are capable of eliciting protective antibodies in laboratory animals. In particular, PsaA has been found by immunological and PCR methods in all *S. pneumoniae* tested including 23 vaccine serotypes as well as clinical isolates from various countries. PsaA has a length of 309 amino acid residues. In an important aspect, the rPsaA used in the immunogenic composition described herein includes at least the amino acid residues at positions 21 to 319 of SEQ ID NO:1.

The capsular polysaccharide (about 300,000 Da) of *N. meningitidis* serogroup C comprises about 850 repeating units of sialic acid with $\alpha(2{\rightarrow}9)$ glycosidic linkage and about 80 percent O-acetylation at C7 or C8. The capsular polysaccharide of *N. meningitidis* serogroup C and PsaA are provided in conjugated form. In a preferred aspect, the capsular polysaccharide and PsaA are conjugated by covalent linkage.

In another aspect, a method is provided for generating an immune response in a subject against pneumococcal surface antigen A (PsaA) and capsular polysaccharide from *N. meningitidis* serogroup C. The method comprises administering to a subject an effective amount for inducing production of antibodies specific to rPsaA and capsular polysaccharide from *N. meningitidis* serogroup C. Administering to a subject a combination of rPsaA and capsular polysaccharide from *N. meningitidis* serogroup C in covalently linked form is effective for generating an immune response in the subject. In an important aspect, immunogenicity of the conjugated pneumococcal surface antigen A (PsaA) and capsular polysaccharide is significantly increased as compared to the immune response observed when the antigens are administered individually. In this aspect, more than a 40-fold increase in immunogenicity is seen for conjugated PsaA as compared to non-conjugated PsaA, and more than a 170-fold increase in immunogenicity is seen for conjugated capsular polysaccharide as compared to non-conjugated capsular polysaccharide.

The immunogenic composition may be administered to a subject by a number of different routes, including intramuscular administration, intranasal administration, oral administration, sub-cutaneous administration, transdermal administration, and transmucosal administration.

Immunogenic compositions described herein are prepared by a method comprising preparing recombinant PsaA ("rPsaA") and conjugating rPsaA with capsular polysaccharide from *N. meningitidis* serogroup C. rPsaA can be prepared using well-known recombinant techniques. Capsular polysaccharide can be isolated from natural sources or synthesized using a number of techniques which are well known in the art.

The immunogenic compositions described herein advantageously provide dual protection against *S. pneumoniae* and *N. meningitidis* infection. The immunogenic composition described herein also utilizes PsaA as a protein carrier for polysaccharide.

Advantageously, the conjugated immunogenic composition provided herein can reduce the costs of preparing and administering the vaccine. This is a particularly important benefit to developing and underdeveloped countries because the vaccine will reduce the economic and medical burden to the countries which have high rates of pneumococcal and meningococcal disease.

BRIEF DESCRIPTION OF THE DRAWINGS

FIG. 1 provides the nucleotide sequence (SEQ ID NO. 2) of a cloned psaA fragment, including restriction endonuclease sites at the 5' and 3' ends produced according to the Example.

FIG. 2 provides the deduced amino acid sequence (SEQ ID NO. 1) of recombinant PsaA protein produced according to the Example.

FIG. 3 shows a photograph of a SDS-polyacrylamide gel electrophoresis and Western blot analysis of rPsaA according to the Example.

DETAILED DESCRIPTION

Figure 4:
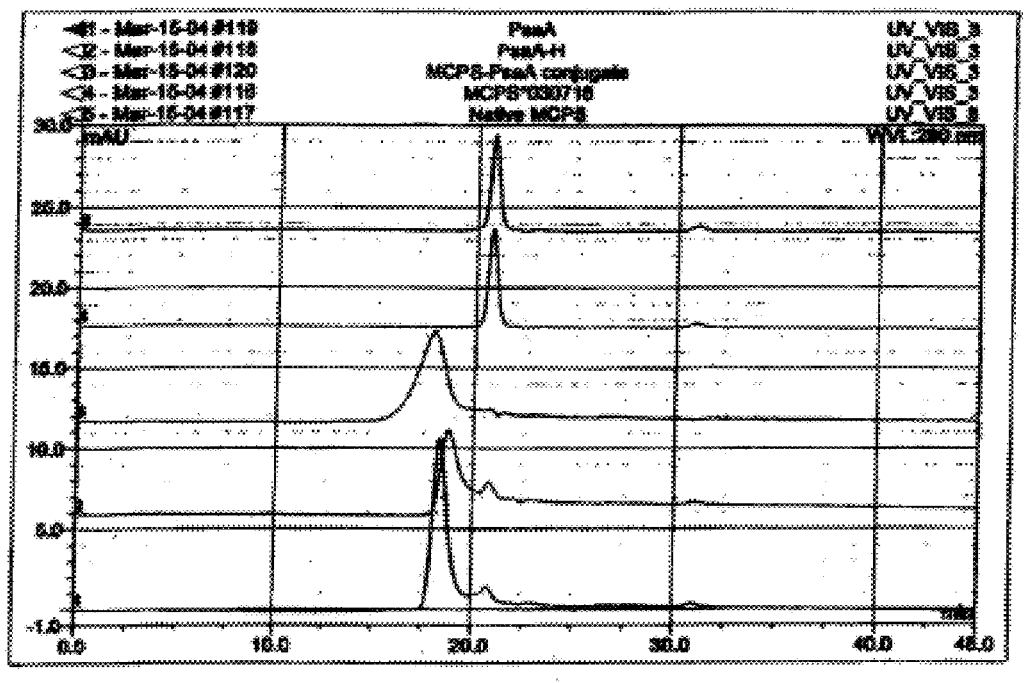
FIG. 4 is a chromatogram demonstrating that the protein signal shifted from a low molecular weight position to a high molecular weight for the conjugate produced according to the Example.

This disclosure provides an immunogenic composition comprising capsular polysaccharide from *N. meningitidis* and a protein from *S. pneumoniae* (referred to as "Pn-Mn" vaccine). In a preferred aspect, the *S. pneumoniae* protein is recombinant pneumococcal surface antigen A ("rPsaA") and the *N. meningitidis* capsular polysaccharide is serogroup C capsular polysaccharide. PsaA is universally found in all tested serotypes of *S. pneumoniae*. The immunogenic composition is useful for inducing production of antibodies for diagnostic and therapeutic purposes. This disclosure further provides an inoculum and vaccine comprising the immunogenic composition dispersed or dissolved in a pharmaceutically acceptable diluent. It is particularly preferred that the rPsaA from *S. pneumoniae* is covalently conjugated to capsular polysaccharide from *N. meningitidis* serogroup C.

The term "antibody" refers to a molecule that is a member of a family of glycosylated proteins called immunoglobulins, which can specifically bind to an antigen. The word "antigen" refers to an entity that is bound by an antibody. "Immunogen" or "immunogenic composition" refers to the entity that induces antibody production or binds to the receptor.

The words "protein" and "polypeptide" are used interchangeably throughout the specification and designate a series of amino acid residues connected by peptide bonds.

Capsular Polysaccharide from *N. Meningitidis* Serogroup C

Polysaccharide is a T cell-independent (T-I) antigen inducing short-term immunity with little immune memory and is not effective in infants younger than 2 years old. When covalently linked to a carrier protein, the resulting PS component in a conjugate vaccine becomes a T cell-dependent (T-D) antigen inducing long-term immunity with immune memory even in infants and young children.

The capsular polysaccharide of *N. meningitidis* serogroup C comprises repeating units of sialic acid with $\alpha$ (2→9) glycosidic linkage and about 80 percent O-acetylation at C7 or C8. The size of the *N. meningitidis* group C polysaccharide is about 590 to about 1,030 sialic acid repeating units assuming the molecular weight of a sialic acid repeating unit is 340 Daltons. The size of the *N. meningitidis* serogroup C capsular polysaccharide particularly useful in the invention is about 200 to about 350 kDa, preferably about 250 to about 300 kDa, although other sizes may be used, if desired, provided that the selected size of the polysaccharide is effective to induce production of antibodies in a subject after conjugation to a carrier protein.

The capsular polysaccharide can be isolated from natural sources using a number of techniques which are well known in the art. For example, *N. meningitidis* group C strain can be grown in a defined medium for 18 hours and inactivated with 0.5 percent formaldehyde. After centrifugation to precipitate the cells, the polysaccharide in the removed supernatant can be precipitated by 0.1 percent cetavlon. The insoluble cetavlon complex is then dissolved in 0.9 M calcium chloride and the crude polysaccharide is precipitated with 5 volume ethanol. The precipitate is further dissolved in phosphate buffer. After phenol extraction and ribonuclease treatment, the sample is dialyzed against water and concentrated (Bundle et al, J. Biol. Chem. 249:4797-4801, 1974, which is incorporated herein by reference.)

In another aspect, the capsular polysaccharide derived from N. meningitidis serogroup C may be substituted with capsular polysaccharide derived from N. meningitidis serogroups A, B, D, X, Y, Z, 29E, W-135, or a combination thereof, in the Pn-Mn conjugates described herein. N. meningitidis serogroups A, B, C, D, X, Y, Z, 29E, and W-135 account for almost all cases of disease. Such conjugates can be administered to a subject capable of inducing an immune response to an antigen in order to provide protection against infection of these serogroups. Meningococcal serogroup A polysaccharide (about 300 kDa) is composed of N-acetyl mannosamine 6-phosphate repeating units with α (1→phosphate) glycosidic linkage and about 70-90 percent O-acetylation at C3. Meningococcal serogroup W135 polysaccharide (~300,000 Daltons) is composed of (2→6) α-D-galactose (1→4) α-D-sialic acid repeating units with about 70 percent O-acetylation at C7 or C9 of the sialic acid residue. Meningococcal serogroup Y polysaccharide (about 300 kDa) is composed of (2→6) α-D-galactose (1→4) α-D-sialic acid repeating units with about 70 percent O-acetylation at C7 or C9 of the sialic acid residue. The size of the N. meningitidis capsular polysaccharide particularly useful in the invention is about 200 to about 350 kDa, preferably about 250 to about 300 kDa, although other sizes may be used, if desired, provided that the selected size of the polysaccharide is effective to induce production of antibodies in a subject after conjugation to a carrier protein. The activation conditions for these polysaccharides may be different from that for group C polysaccharide due to differences in their structures.

Pneumococcal Protein

PsaA has a length of 309 amino acid residues. It is preferred that the rPsaA used in the immunogenic composition includes at least the residues at positions 21 to 319 of SEQ ID NO:1.

Recombinant PsaA from S. pneumoniae can be prepared using conventional recombinant techniques. Recombinant methodologies required to produce a DNA encoding a desired protein are well known and are routine to those of ordinary skill in the art. The nucleic acid sequences used to practice this invention, whether cDNA, genomic DNA, vectors, and the like, may be isolated from a variety of sources, genetically engineered, amplified, and/or expressed recombinantly. The nucleotide sequence for psaA is provided at nucleotide positions 6 to 867 in SEQ ID NO:2. The coding sequence of the desired protein can be cloned into a vector.

Any recombinant expression system can be used, including bacterial, mammalian, yeast, insect, or plant cell expression systems. Alternatively, these nucleic acids can be synthesized in vitro by well-known chemical synthesis techniques. Double stranded DNA fragments may then be obtained either by synthesizing the complementary strand and annealing the strands together under appropriate conditions, or by adding the complementary strand using DNA polymerase with an appropriate primer sequence.

Nucleic acid amplification methods are well known in the art. Oligonucleotide primers can be used to amplify nucleic acids to generate psaA coding sequence used to prepare recombinant PsaA. The coding sequence can be cloned into an expression cassette, such as plasmids, recombinant viruses which can infect or transfect cells in vitro, ex vivo, and/or in vivo, and other vectors which can be used to express the PsaA polypeptide in vitro or in vivo. Selection markers can be incorporated to confer a selectable phenotype on transformed cells, such as antibiotic resistance. The expressed rPsaA can be recovered and purified using conventional techniques.

In another aspect and in addition to PsaA, other pneumococcal proteins can be used as a component of the Pn-Mn conjugate vaccine provided herein. Other S. pneumoniae proteins that may be used include pneumolysin, pneumococcal surface protein A (PspA), pneumococcal surface protein C (PspC or CbpA), pneumococcal histidine triad proteins or similar proteins with different nomenclatures such as PhtA or BVH11-3, PhtB or PhpA or BVH-11, PhtE or BVH-3), PhtD or BVH-11-2, and, pneumococcal choline binding protein A (PcpA), non-heme iron-containing ferritin or pneumococcal protective proteins (PppA, Dpr), neuraminidase A (NanA), neuraminidase B (NanB), iron transport proteins or iron-compound-binding protein PiuA and PiaA, N-acetylmuramoyl-L-alanine amidase or autolysin (LytA), endo-β-acetylglucosaminidase (LytB), 1,4-β-N-acetylmuranminidase (LytC), caseinolytic protease or serine proteases (ClpP), and adherence and virulence protein A (PavA).

Conjugate Preparation

Polysaccharides contain hydroxyl groups, and occasionally carboxyl and amino groups, and proteins contain amino and carboxyl groups. Both polysaccharides and proteins are not active for chemical reaction with each other in their natural form. Proper pretreatment or activation of one or both of the polysaccharide and protein is required to convert the otherwise non-reactive molecules to a reactive form in order to produce the polysaccharide-protein conjugate. Many methods are known in the art for conjugating a protein to a polysaccharide. Polysaccharide can be activated by cyanogen bromide to provide cyanate groups which react with hydrazide-activated protein (Schneerson et al., J. Exp. Med. 1980; 152:361-3760). Polysaccharide can be activated by cyanogen bromide to provide cyanate groups, which further reacts with di-hydrazide, and then conjugates to protein in the presence of EDC (Chu et al., Infect. Immun 1983; 40:245-256). Polysaccharide can be partially hydrolyzed and added with an amino group at the reducing terminus. After a bifunctional linker is added to the amino group, the activated polysaccharide is conjugated to the carrier protein (Costantino et al., Vaccine 1992; 10:691-8). Polysaccharide can be activated with 1-cyano-4-dimethylaminopyridinium tetrafluoroborate to provide cyanate groups which react with a carrier protein (Lees A, Nelson B L, Mond J J. Vaccine 1996; 14:190-198).

In a preferred aspect, rPsaA is dialyzed before use, such as against 30 mM NaCl at about 4° C. for about 18 to about 24 hours. The dialyzed rPsaA is then treated to activate the protein, such as with 0.1 M MES (pH 6.5), 0.5 M hydrazine (pH 7.0), and 20 mM 1-[3-dimethylamino propyl)-3-ethyl carbodiimide-HCl ("EDC" from Sigma-Aldrich) in saline, and incubated for 4 hours. The treated rPsaA is then neutralized, such as with 1 M NaOH, before dialyzing the protein, such as dialyzing against buffer containing 3 mM $Na_2CO_3$ and 30 mM NaCl at 4° C. The dialyzed activated rPsaA can be used immediately or stored at 4° C.

In a preferred aspect, the capsular polysaccharide is treated with 6 mM sodium periodate and incubated for 4 hours at room temperature to activate the capsular polysaccharide. The activated capsular polysaccharide is then dialyzed against deionized water, such as for about 18 to about 24 hours at 4° C. The dialyzed activated capsular polysaccharide can be used immediately or stored at 4° C.

Activated rPsaA is lyophilized, redissolved in water. Dialyzed activated capsular polysaccharide (is lyophilized, redissolved in 0.2 M HEPES, pH 7.5, 30 mM EDTA. The protein solution is added to the polysaccharide solution and incubated overnight. $NaBH_4$ is added to a final concentration of 50 mM and incubated for about 4 to about 6 hours to reduce the C═N double bonds in the polysaccharide-protein conjugate to C—N single bonds, and to reduce the unreacted aldehyde to alcohol. The conjugate is dialyzed against 150 mM NaCl, 10 mM HEPES (pH 7), 1 mM EDTA at 4° C. The dialyzed conjugate can then be evaluated, such as by HPLC, for shift of protein signal (280 nm) from 19 minute position to 18 minute upon conjugation.

Method of Using Conjugate

The rPsaA/capsular polysaccharide conjugate provided herein can be administered to a subject capable of inducing an immune response to an antigen. The rPsaA/capsular polysaccharide conjugate is administered to the subject in an effective amount for inducing an antibody response. An "effective amount" is an amount of rPsaA/capsular polysaccharide conjugate which assists a subject in producing both anti-rPsaA and anti-capsular polysaccharide antibodies. Such antibodies may prevent infection by S. pneumoniae and N. meningitidis serotype C.

One of ordinary skill in the art can determine whether an amount of the rPsaA/capsular polysaccharide conjugate is effective to induce immunity in a subject using routine methods known in the art. For example, the ability of an antigen to produce antibody in a subject can be determined by screening for antibodies using separate coating antigens rPsaA and capsular polysaccharide in the respective ELISA assays.

In one aspect, a vaccine formulation is provided for N. meningitidis serogroup C and S. pneumoniae. The vaccine formulation is effective for generating an immune response in a subject to both N. meningitidis serogroup C and S. pneumonia. The vaccine formulation comprises rPsaA from S. pneumoniae and capsular polysaccharide from N. meningitidis serogroup C. The conjugated immunogenic composition can be provided with one or more additional components, such as a pharmaceutically acceptable diluents, carriers, adjuvants, and/or buffers. For example, the conjugate can be dispersed or dissolved in a diluent.

The immunogenic composition may be prepared as a solution, suspension, tablet, pill, capsule, sustained release formulation, powder, or the like. The antigens and immunogenic composition may be mixed with physiologically acceptable carriers which are compatible therewith. These may include water, saline, dextrose, glycerol, ethanol, combinations thereof, and the like. The vaccine may further contain auxiliary substances, such as wetting or emulsifying agents or pH buffering agents, to further enhance the effectiveness. Administration of the conjugate in a vaccine formulation can include delivery by various routes, such as, for example, oral, intravenous, intramuscular, nasal, subcutaneous, and intraperitoneal administration.

The immunogenic composition is administered in a manner compatible with the dosage formulation, and in such amount as to be therapeutically effective, protective, and immunogenic. The quantity to be administered depends on the subject to the immunized, including, for example, the capacity of the subjects immune system to synthesize antibodies and, if needed, to produce a cell-mediated immune response. Precise amounts of antigen and immunogenic composition to be administered depend on the judgment of the practitioner. However, suitable dosage ranges are readily determinable by those skilled in the art and may be of the order of micrograms to milligrams. Suitable regimes for initial administration and booster doses are also variable but may include an initial administration followed by subsequent administrations. The dosage of the vaccine may also depend on the route of administration and will vary according to the size of the subject.

In an important aspect, the rPsaA/capsular polysaccharide Pn-Mn conjugate provided herein may be used to prevent infection of both S. pneumoniae and N. meningitidis serotype C, which are the leading causes of otitis media and meningitis in young children. Furthermore, the rPsaA/capsular polysaccharide conjugate provided herein also could be used in the prevention of other pneumococcal and meningococcal diseases, such as bacteremia, pneumoniae and meningitis in the population of other age groups.

The examples that follow are intended to illustrate the invention and not to limit it. All percentages used herein are by weight unless otherwise indicated. All patents, patent applications, and literature references cited herein are hereby incorporated by reference in their entirety.

EXAMPLE

A better understanding of the vaccine provided herein and its many advantages is provided with the following example.

A. Preparation of Purified rPsaA psaA gene cloning and expression. To prepare recombinant pneumococcal PsaA (rPsaA) protein, the coding sequence of pneumococcal psaA genes in E. coli was cloned in the expression vector pET22b(+) (Novagen, Madison, Wis.). Sequence analysis revealed that the coding sequence of psaA does not include BamHI and HindIII restriction sites. For the purpose of cloning, expression, and purification of rPsaA protein, a pair of primers for PCR amplification were designed so that: 1) the PCR product would have a BamHI and HindIII site at the 5' and 3' ends, respectively; 2) the reading frame of cloned psaA would be in-frame with that of the vector; and 3) the produced rPsaA protein would have a His-tag at its C-terminal. The forward and reverse primers (5'-G GGATCCTAGCGGAAAAAAAGATACA-3' (SEQ ID NO:3), 5'- GCAAGCTTTGCCAATCCTTCAGCAATC-3' (SEQ ID NO:4), respectively, were intended to amplify a 868-bp fragment starting from nucleotide no. 42 to no. 921 of the psaA coding sequence. The underlined nucleotides indicate the positions of BamHI and HindIII sites in thee primers. The coded rPsaA protein would have 331 amino residues and a predicted molecular mass of 36,940 daltons. The nucleotide sequence of the cloned fragment is shown in FIG. 1 and the predicted amino acid sequence for rPsaA in FIG. 2.

A typical PCR mixture contained 5 µmole primers, 20 ng S. pneumoniae serotype 4 chromosomal DNA and PCR Supermix (Life Technologies, Rockville, Md.). The conditions for PCR were as follows: DNA denaturation at 95° C. for 40 seconds, primer annealing at 42° C. for 1 min, and DNA synthesis at 72° C. for 1.5 min. After 30 cycles of synthesis, the reaction was terminated with an extension at 72° C. for 5 min. The PCR products were purified with the GeneClean kit (Qbiogen, Carlsbad, Calif.), cloned into pGEM-T easy vector (Promega, Madison, Wis.) and transformed into E. coli DH5α. The insert was isolated from the resultant plasmid after a double digestion with restriction enzymes BamHI and HindIII, cloned into the compatible site of pET22b(+) to generate plasmid pST648, and transformed into E. coli BL21 (DE3). To confirm that psaA gene on pST648 was cloned as planned, the restriction map of the cloned PCR product was determined. The results were consistent with those of published psaA gene. The proper cloning of the BamHI-HindIII restriction fragment into pET22b(+) was further confirmed by the induction of recombinant protein and by the presence of His-tag at the carboxyl end.

To induce the synthesis of recombinant protein, isopropyl-13-D-thiogalactoside (IPTG, 0.1 mM) was added to the log-phase culture (A600 $nm^{=0.6}$) of E. coli BL21(DE3) harboring pST648 and growth continued for another 2 hours. Cells were harvested, washed, suspended in one-tenth volume of 50 mM Tris-HC1, pH 7.9 containing 200 mM NaCl (TN buffer) at 4°

C., and disrupted by sonication. After the removal of unbroken cells by centrifugation, the supernatant was subject to SDS-PAGE analysis. To confirm that recombinant protein had a His-tag, the proteins on the SDS-gel were analyzed by western blotting against mouse monoclonal anti-poly-histidine antibody (Sigma-Aldrich, St. Louis, Mo.). The proteins on the gel were transferred onto nitrocellulose paper and the paper was washed with blotto (20 mM Tris, 0.2M NaCl, 1.5 percent nonfat milk), incubated with monoclonal anti-poly-histidine antibody in blotto (1:200 dilution) for 2 hours, washed with blotto three times, incubated with alkaline phosphatase-conjugated goat anti-mouse antibody in blotto (1:5000 dilution), and washed with blotto and AP buffer (0.1 M NaCl, 0.1 M Tris-Cl, pH 9.5). The antibody-antigen interaction was visualized by incubating with 0.1 percent naphthol and 1 percent fast blue (Sigma-Aldrich). The results are shown in FIG. 3. The results indicate that the overproduced protein was indeed rPsaA and the crude cell lysate of *E. coli* BL21(DE3)(pST648) could be used as the source of rPsaA in protein purification.

Purification of rPsaA protein. To purify rPsaA protein, crude cell lysate was loaded on a HIS-BIND® Column (Novagen, Madison, Wis.). The resin was washed with binding buffer (TN buffer containing 50 mM imidazole) and washing buffer (TN buffer containing 200 mM imidazole) to remove excess and nonspecifically bound proteins. The bound protein was eluted with elution buffer (TN buffer containing 1 M imidazole) and analyzed by SDS-polyacrylamide gel electrophoresis and Western blotting against monoclonal anti-poly-histidine antibody as described above. Fractions containing protein that reacts with anti-poly-histidine monoclonal antibody were collected as purified rPsaA protein (FIG. 3).

B. Preparation of rPsaA-MCPS Conjugate

Activation of rPsaA. rPsaA was dialyzed against 30 mM NaCl at 4° C. overnight before use. The dialyzed rPsaA was mixed with 1 M MES, pH 6.5, 5 M hydrazine, pH 7.0, 1 M EDC (Sigma-Aldrich) in saline at the final concentration of 0.1 M, 0.5 M, and 20 mM, respectively. After incubation at room temperature for 4 hours, 1 M NaOH (0.05 mL) was added to neutralize the reaction before dialysis against buffer containing 3 mM $Na_2CO_3$ and 30 mM NaCl at 4° C. The protein solution was stored at 4° C.

MCPS activation. *N. meningitidis* type C capsular PS (MCPS, 10 mg/ML) was mixed with sodium periodate at a final concentration of 6 mM. After incubation at room temperature for 4 hours, the reaction mixture was dialyzed against deionized water overnight and stored at 4° C.

Conjugation of PsaA-MCPS. Aliquot activated rPsaA (0.25 mg) was lyophilized and re-dissolved in 25 µl water. Aliquot activated MCPS (0.25 mg) was lyophilized and redissolved in 25 µl of 0.2 M HEPES, pH 7.5 containing 30 mM EDTA. These two solutions were combined. After incubation overnight at room temperature, 5 µl of 1 M $NaBH_4$ was added and incubation continued for another 6 hours. After dialysis against 150 mM NaCl, 10 mM HEPES, pH 7, 1 mM EDTA at 4° C., the conjugate product was stored at 4° C. The conjugate of MCPS with rPsaA was evaluated with HPLC analysis using a Waters Ultrahydrogel Linear size-exclusion column and monitored at the wavelengths of 206 nm and 280 nm. Upon conjugation, the protein signal shifted from low molecular weight position to the high molecular weight in the chromatogram, as shown in FIG. 4.

C. Characterization of rPsaA-MCPS Conjugate.

Immunogenicity. Mice (NIH-Swiss) were subcutaneously immunized every two weeks with rPsaA, MCPS, or PsaA-MCPS conjugate, respectively, at the dose of 1 µg per mouse. Blood was collected from optical vein two weeks after the third immunization and the titers of antibodies were determined by enzyme-linked immunosorbent assay (ELISA). Briefly, wells of microliter plate (Dynatec, no.1) was coated with MCPS by adding 100 µl of solution comprised of antigen, 0.5 µg/mL rPsaA or 5 µg/mL native MCPS plus 5 mg/ml methylated human serum albumin in PBS, pH 7.5 and incubated at room temperature for at least 4 hours. Wells were washed three times (150 µl/well) with PBS containing 0.05 percent TWEEN® 20 and 0.02 percent $NaN_3$. 100 µL of diluent (5 percent calf serum and 0.02 percent $NaN_3$ in PBS) was added to each well and a two-fold serial dilution of diluted (1:100) antiserum was prepared. The reference serum, which was assigned with 3,200 units/mL IgG against MCPS or rPsaA, was similarly treated in the same plate. After incubating overnight at room temperature and washing three times, 100 µl of alkaline phosphate-conjugated goat anti-mouse IgG Fc (1:3000 dilution) was added and incubated at room temperature for 3 hours. Wells were washed three times and 100 µl of substrate (p-nitrophenyl phosphate, 1 mg/mL in 1 M Tris-HCl, pH 9.8 containing 0.3 mM $MgCl_2$) was added. The plate was incubated at room temperature for 20 minutes (it might vary depending on the color development of sample and reference serum) and the absorbances were measured at 405 nm. The respective reference serum for MCPS and rPsaA was prepared in the laboratory and were used as standards to determine the antibody level of the sample serum. Results are shown in Table I below.

TABLE I

Immunogenicity of rPsaA, MCPS, and rPsaA-MCPS conjugate.

| Antigen | Dose | IgG level* | |
|---|---|---|---|
| | | anti-PsaA | anti-MCPS |
| rPsaA | 3 × 1 µg | 107 (9; 1678) | — |
| MCPS | 3 × 1 µg | — | 533 (46; 6176) |
| rPsaA-MCPS | 3 × 1 µg | 4,418 (2006; 9734) | 90,506 (50,421; 162,455) |

*The data that is not in parenthesis represents the geometric mean of IgG antibody level in 10 antiserum samples. The anti-rPsaA or anti-MCPS IgG antibody level of each antiserum was measured by ELISA and compared with respective reference serum, assigned with 3,200 unit/mL IgG antibody. The numbers in parenthesis represents the confidence interval of one standard deviation.

Both rPsaA and MCPS were immunogenic in mice in the absence of adjuvant. Their immunogenicity increased significantly after they were conjugated. When compared with each individual component, the immunogenicity increased approximately 41-fold and 170-fold for rPsaA and MCPS, respectively.

Figure 5A:
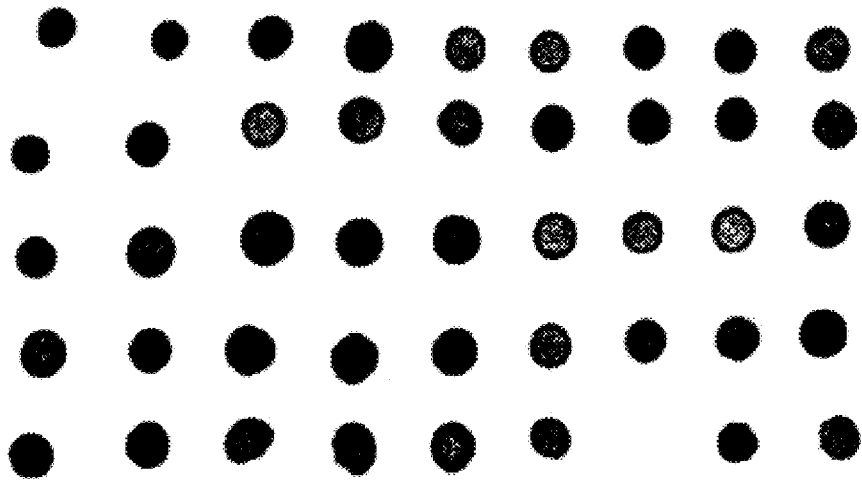
FIG. 5A shows a photograph of an Immuno-dot blot according to the Example.
Figure 5B:
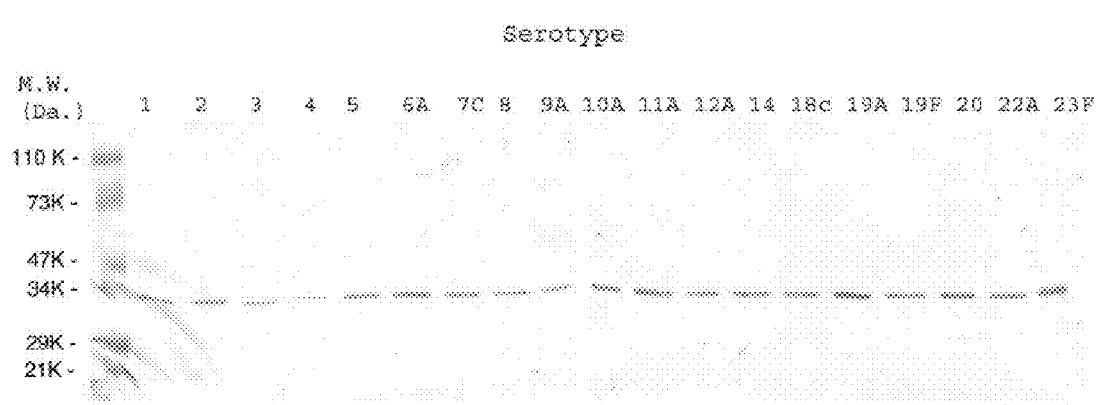
FIG. 5B shows a photograph of a Western blot according to the Example.

Reactivity of anti-rPsaA antibodies. It has been demonstrated that active immunization of PsaA is effective to protect laboratory animals from *S. pneumoniae* infection. To provide protection, anti-PsaA should interact with all *S. pneumoniae* cells. The cross-reactivity of the generated anti-rPsaA antibodies was investigated by immuno-dot blotting and western blotting against clinical isolates of *S. pneumoniae*, including serotypes 1, 2, 3, 4, 5, 6A, 6B, 7C, 8, 9A, 10A, 10B, 11A, 12A, 14, 15A, 15C, 16F, 18A, 18C, 19A, 19F, 20, 24, 22A, 23B, 23F, 23C and 35. Cells of *S. pneumoniae* were cultured in 15 mL Todd-Hewitt broth overnight at 37° C. in the presence of 5 percent $CO_2$, harvested by centrifugation, and suspended in 2 mL of TN buffer. Cells were disrupted by sonication in ice bath at the energy level of 7, 50 percent cycle, for 5 minutes. The supernatant after centrifugation at 10,000×g for 10 minutes was collected and used as the source of *S. pneumoniae* proteins. For immuno-dot blotting, 5 µl cell lysate was spotted on the nitrocellulose paper. For Western blot, randomly selected pneumococcal cell lysates were analyzed by SDS-PAGE and transferred on nitrocellulose paper. The paper was processed as described above, except anti-rPsaA antibody was used. Results are shown in FIG. 5A and FIG. 5B. The anti-rPsaA antibody cross-reacted with cells of all serotypes tested and reacted with a single protein that has an apparent molecular weight comparable to that of PsaA.

Bactericidal activity of anti-MCPS antibody. The biological function of the induced MCPS-specific antibodies was determined by bactericidal assay against *N. meningitidis* serogroup C (strain C11). Briefly, bacteria were cultured overnight on brain heart infusion (BHI) agar plates containing 5 percent normal horse serum (NHS) and transferred to fresh plates and cultured for 5 hours the second day. Bacteria from the 5 hour culture were suspended to 65-66 percent transmittance at 530 nm in DPBSG (1×PBS, pH 7.2, 0.5 mM $MgCl_2$, 0.9 mM $CaCl_2$, and 0.01 percent gelatin) followed by 1:10,000 dilution with the same buffer to contain approximately 4,000 cfu/mL. In the wells of a microtiter plate, 50 µl 2-fold dilutions of test and control sera were prepared with DPBSG and mixed with 25 µl bacterial suspension and 25 µl baby rabbit complement (Pel-Freez, Rogers, Ark.). After incubation at 37° C. for 60 min, 10 µl of the bacterial suspension was withdrawn from each well and spread on the BHI/NHS plate. The colonies were enumerated after incubation overnight at 37° C. with 5 percent $CO_2$. The bactericidal titer was the reciprocal of the highest dilution of the sample yielding a 50 percent reduction in CFU as compared to the control well containing complement without antiserum. The geometric means of the titer for each mouse group was calculated. Results are shown in Table II below.

TABLE II

Bactericidal activity of antisera against MCPS, rPsaA-MCPS conjugate.

| Antigen | Bactericidal activity titer* |
|---|---|
| MCPS | 109 (63; 190) |
| rPsaA-PCPS | 5022 (1123; 22454) |

*The data that is not in parenthesis represents the geometric mean of sera from 10 mice for each antigen. The numbers in parenthesis represents the confidence interval of one standard deviation.

Sera for both MCPS and rPsaA-MCPS conjugates had bactericidal activity, but the titer for the conjugates were significantly higher (approximately 46-fold).

While the invention has been particularly described with specific reference to particular process and product embodiments, it will be appreciated that various alterations, modifications, and adaptations may be based on the present disclosure, and are intended to be within the spirit and scope of the invention as defined by the following claims.

What is claimed is:

1. An immunogenic composition comprising isolated capsular polysaccharide from serogroup C *Neisseria meningitidis*, wherein the capsular polysaccharide is conjugated to purified pneumococcal surface antigen A (PsaA), the PsaA being 309 amino acid residues in length, wherein the immunogenic composition generates a murine serum IgG response to both the serogroup C *Neisseria meningitidis* and the PsaA when administered to mice in an immunogenically effective amount, the murine serum IgG response generated to the serogroup C *Neisseria meningitidis* and the PsaA being greater than murine serum IgG immune response generated by each of the serogroup C *Neisseria meningitidis* and the PsaA in a non-conjugated form.

2. An immunogenic composition comprising isolated capsular polysaccharide from serogroup C *Neisseria meningitidis*, wherein the capsular polysaccharide is conjugated to purified pneumococcal surface antigen A (PsaA), the PsaA being a recombinant PsaA that comprises at least amino acid residues 21 to 319 of SEQ ID NO: 1, wherein the immunogenic composition generates a murine serum IgG response to both the serogroup C *Neisseria meningitidis* and the PsaA when administered to mice in an immunogenically effective amount, the murine serum IgG immune response generated to the serogroup C *Neisseria meningitidis* and the PsaA being greater than murine serum IgG immune response generated by each of the serogroup C *Neisseria meningitidis* and the PsaA in a non-conjugated form.

3. The immunogenic composition of claim 1 or 2 further comprising one or more pharmaceutically acceptable diluents, carriers, adjuvants, and/or buffers.

4. The immunogenic composition of claim 2, wherein the immunogenic composition elicits a bactericidal immune response in said mice against serogroup C *Neisseria meningitidis*.

5. A method comprising administering to a subject an amount of the immunogenic composition of claim 1, 2 or 3.

* * * * *